United States Patent [19]

Toja et al.

[11] Patent Number: 4,902,699
[45] Date of Patent: Feb. 20, 1990

[54] OXIME OF 1, 2, 5, 6-TETRAHYDROPYRIDINE COMPOUNDS THEIR USE AS MEDICAMENTS AND THE COMPOSITIONS CONTAINING THEM

[75] Inventors: Emilio Toja, Milan; Carla Bonetti, Fontanella; Fernando Barzaghi; Giulio Galliani, both of Monza, all of Italy

[73] Assignee: Roussel Uclaf, Paris, France

[21] Appl. No.: 234,627

[22] Filed: Aug. 22, 1988

[30] Foreign Application Priority Data

Aug. 21, 1987 [IT] Italy .................................. 21691

[51] Int. Cl.⁴ .................... A61K 31/44; C07D 211/70
[52] U.S. Cl. .................... 514/357; 546/334; 546/336; 546/337; 546/338
[58] Field of Search ............ 546/335, 338, 334, 336, 546/337; 514/357

[56] References Cited

U.S. PATENT DOCUMENTS 3,004,979 10/1961 Druey et al. ................. 546/338
4,710,508 12/1987 Bergmeier et al. ............ 514/357

FOREIGN PATENT DOCUMENTS 0725633 1/1966 Canada ....................... 546/338
1258847 3/1961 France ....................... 546/336

OTHER PUBLICATIONS

Jaffé *Journal of the American Chemical Society*, vol. 76, No. 13, Jul. 5, 1954, pp. 3527-3531.
Chemical Abstracts, vol. 92, No. 13, Mar. 31, 1980, p. 641, Abstract No. 110798y.

*Primary Examiner*—Mary C. Lee
*Assistant Examiner*—Zinna Northington-Davis
*Attorney, Agent, or Firm*—Stevens, Davis, Miller & Mosher

[57] ABSTRACT

Compounds useful in the treatment of patients suffering from senile dementia, Alzheimer's disease or memory defects, of the formula

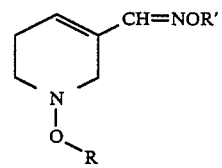

in which R represents hydrogen or a linear, branched or cyclic alkyl, alkenyl, or alkynyl, containing up to 8 carbon atoms, or the radical

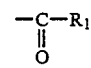

in which $R_1$ represents a linear or branched, alkyl, alkenyl or alkynyl, containing up to 8 carbon atoms, a linear or branched, saturated or unsaturated, alkoxy containing up to 8 carbon atoms, or aryl containing up to 14 carbon atoms, or the radical

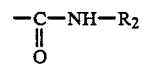

in which $R_2$ represents a linear or branched alkyl, alkenyl or alkynyl, containing up to 8 carbon atoms, aryl containing up to 14 carbon atoms, possibly substituted, or aralkyl containing up to 18 carbon atoms, possibly substituted, and R' represents a linear, branched or cyclic alkyl, alkenyl or alkynyl, containing up to 8 carbon atoms, as well as their addition salts with organic or mineral acids.

10 Claims, No Drawings

OXIME OF 1, 2, 5, 6-TETRAHYDROPYRIDINE COMPOUNDS THEIR USE AS MEDICAMENTS AND THE COMPOSITIONS CONTAINING THEM

The present invention relates to new derivatives of the oxime of 1,2,5,6-tetrahydropyridin-3-carboxaldehyde, the process for their preparation, their use as medicaments and compositions containing them.

The subject of the invention is the compounds of the formula (I):

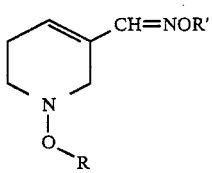

in which R represents either hydrogen, or a linear, branched or cyclic alkyl, alkenyl, or alkynyl, containing up to 8 carbon atoms, or the radical

in which $R_1$ represents a linear or branched alkyl, alkenyl or alkynyl containing up to 8 carbon atoms, a linear or branched, saturated or unsaturated, alkoxy containing up to 8 carbon atoms, or aryl containing up to 14 carbon atoms, or the radical

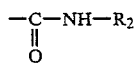

in which $R_2$ represents a linear or branched alkyl, alkenyl or alkynyl, containing up to 8 carbon atoms, aryl containing up to 14 carbon atoms, possibly substituted, or aralkyl containing up to 18 carbon atoms, possibly substituted, and R' represents a linear, branched or cyclic alkyl, alkenyl or alkynyl, containing up to 8 carbon atoms, as well as their addition salts with organic or mineral acids.

Among the addition salts with acids, there can be cited those formed with mineral acids, such as hydrochloric, hydrobromic, sulphuric or phosphoric acids, or with organic acids such as formic, acetic, propionic, benzoic, maleic, fumaric, succinic, tartaric, citric, oxalic, glyoxylic, aspartic, alkanesulphonic, such as methane- or ethanesulphonic, arylsulphonic such as benzene- or paratoluenesulphonic acids.

When R, $R_1$, $R_2$ or R' represents a linear or branched alkyl, it is preferred to be methyl, ethyl, n-propyl, isopropyl, n-butyl, isobutyl, n-pentyl, n-hexyl, tert-butyl, tert-pentyl, neopentyl or n-hexyl.

When R, $R_1$, $R_2$ or R' represents alkenyl or alkynyl, it is preferred to be an ethylene radical such, for example, as vinyl, allyl, 1,1-dimethylallyl or but-2-enyl, or an acetylene radical such, for example, as ethynyl or propynyl.

When R or R' represents a cyclic alkyl, it is preferred to be cyclopropyl, cyclobutyl, cyclopentyl, cyclohexyl, cyclopropylmethyl, cyclobutylmethyl, cyclopentylmethyl or cyclohexylmethyl.

When $R_1$ or $R_2$ represents aryl, it is preferred to be phenyl.

When $R_2$ represents aralkyl, it is preferred to be phenalkyl, particularly benzyl or phenethyl.

The aryl or aralkyl can include one or more substituents chosen from halogen, alkyl containing up to 8 carbon atoms, or alkoxy containing up to 8 carbon atoms.

By halogen, there is preferred chlorine or bromine, by alkyl there is preferred methyl, ethyl linear or branched propyl, linear or branched butyl, and by alkoxy, there is preferred methoxy, ethoxy, propoxy or butoxy.

Among the preferred compounds of the invention, there can be cited the compounds in which R represnnts hydrogen, the radical —COCH$_3$, the radical

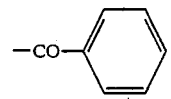

or the radical —CONH—$R_2$ in which $R_2$ represents butyl, phenyl, 4-methoxyphenyl, 4-chlorophenyl or 4-isopropylphenyl.

There can also be cited the compounds in which R' represents CH$_3$ or CH$_2$C≡CH.

Naturally, the invention has more particularly as its subject the compounds with the formula (I) of which the preparation is given further on in the examples.

Among these compounds, there can be cited the products of examples 1, 3, 4, 7, 10, 13, 15, 16, and quite particularly the methyl ether of (4-chlorophenyl)-amino-carbonyloxy-1,2,5,6-tetrahydropyridin-3-carboxaldehyde oxime, as well as their addition salts with acids.

The compounds of the invention present very interesting pharmacological properties and notably an important cholinomimetic activity by oral route which has a long duration of action.

It is well known that difficulties of learning and of memory in elderly persons are connected above all with a defect of the central cholinergic system, in particular in senile dementia and Alzheimer's disease.

It is therefore evident that products having a central cholinergic action can be employed in therapeutic treatment of these maladies (Bartus, R. I. Science 217, 408, 1982).

It has been shown that arecoline injected by intravenous route has a positive effect on patients having a memory defect (Sitaram N. et al., Science 201, 274, 1978) (Christie J. E. et al., Brit. J. Psychiatry, 138, 46, 1981).

A limitation to the therapeutic use of arecoline is connected with the fact that this product has a very weak activity by oral route and a short duration of action.

The products which are the subject of the invention have shown, after administration by oral route, a central cholinomimetic activity up to 1000 times greater than that of arecoline and a longer duration of action.

Therefore the invention has as its subject the invention products as medicaments useful in particular in the treatment of Alzheimer's disease or senile dementia and also in the treatment of memory defects.

The preferred medicament is the compound of example 14.

The usual posology is variable according to the affection concerned, the subject treated and the administration route, it can be between 1 mg and 100 mg/day, preferably between 1 mg and 20 mg/day, for example, between 1 and 25 mg/day in one or more doses for the product of example 14 administered by oral route.

The present invention also has as its subject the pharmaceutical compositions containing at least one compound of the formula (I) as active principle.

The pharmaceutical compositions according to the invention can be solid or liquid and are presented in the pharmaceutical forms currently used in human medicine, such, for example, as plain or sugar-coated tablets, capsules, granules, suppositories and injectable preparations; they are prepared according to the usual methods.

The active principle or principles can be incorporated in them with the excipients usually employed in these pharmaceutical compositions, such as talc, gum arabic, lactose, starch, magnesium stearate, cocoa butter, aqueous or nonaqueous vehicles, fatty substances of animal or vegetable origin, paraffin derivatives, glycols, the various wetting, dispersing or emulsifying agents and preservatives.

The invention also has as its subject a process for the preparation of the compounds with the formula (I) characterized in that a compound with the formula (II):

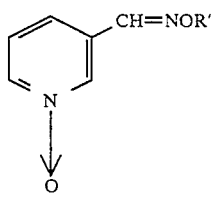
(II)

in which R' has the previously indicated significance, is submitted to the action of a reducing agent in order to obtain the compound with the formula ($I_A$) corresponding to the compound with the formula (I) in which R represents hydrogen

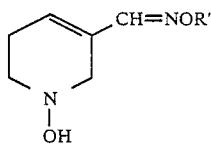
($I_A$)

which, if desired, is submitted to the action of an esterification, etherification, alkoxycarbonylation or amidification agent in order to obtain the corresponding derivative with the formula (I) which, if desired, is submitted to the action of an acid in order to form its salt.

In a preferred way of carrying out the invention process:
the hydrogenation agent is sodium hydroboride;
the esterification agent is an acid halide;
the etherification agent is a dialkyl sulphate;
the alkoxycarbonylation agent is an alkyl chloroformate:
the amidification agent is an alkyl, aryl or aralkyl isocyanate.

The products with the formula (II) used as starting products are known in a general way. Certain of them are described in J. Heterocyclic Chem., 16, 1459 (1979).

The following examples illustrate the invention, nevertheless without limiting it.

EXAMPLE 1

Hydrochloride of the methyl ether of 1-hydroxy-1,2,5,6-tetrahydropyridin-3-carboxaldehyde oxime.

1.2 g of N-oxide-pyridin-3-carboxaldehyde-O-methyloxime (J. Het. Chem. 16, 1459 (1979)) is dissolved in 40 cm$^3$ of methanol, cooled to $-10°$ C., 0.9 g of sodium borohydride is added and the whole is agitated at ambient temperature for 1 hour, then concentrated under reduced pressure, taken up with water, and extracted with ether. After evaporating and chromatographing on silica, eluting with ethyl acetate, 0.87 g of an oil is obtained which is converted into the hydrochloride. By crystallizing from a mixture of isopropanol and ether, 0.9 g of the expected hydrochloride is obtained. m.p. 146°–147° C.

| Analysis: | | | | | | | |
|---|---|---|---|---|---|---|---|
| Calculated: | C % | 43.64 | H % | 6.80 | N % | 14.54 |
| Found: | | 43.85 | | 6.76 | | 14.52 |

EXAMPLE 2

Hydrochloride of the methyl ether of 1-methoxy-1,2,5,6-tetrahydropyridin-3-carboxaldehyde oxime To 3 g of (N-hydroxy) 1,2,5,6-tetrahydropyridin-3-carboxaldehyde-O-methyloxime dissolved in 45 cm$^3$ of tetrahydrofuran, cooled to 0° C., there is added 0.93 g of sodium hydride at 55% in oil, and cooling to 0° C. for 15 minutes; 2.42 g of dimethyl sulphate is added, agitation is maintained at 0° C. for 15 minutes, then at ambient temperature for 1 hour, followed by evaporating to dryness; the residue is purified by chromatography on silica (eluent: ethyl acetate, then chloroform-methanol 7-3, then methanol alone). After evaporating to dryness, the oily residue is taken up with methanol and salified by means of gaseous hydrochloric acid, then crystallized from isopropyl alcohol, so obtaining 1.8 g of the expected hydrochloride. m.p. 176° C. (decomposes).

| Analysis: $C_8H_{14}N_2O_2$, HCl. | | | | | | | |
|---|---|---|---|---|---|---|---|
| Calculated: | C % | 46.79 | H % | 7.440 | N % | 13.60 |
| Found: | | 46.49 | | 7.32 | | 13.56 |

Soluble in $H_2O$, 2N HCl and 2N NaOH.

EXAMPLE 3

Hydrochloride of the methyl ether of 1-acetoxy-1,2,5,6-tetrahydropyridin-3-carboxaldehyde oxime To 3.8 g of (1-hydroxy) 1,2,5,6-tetrahydropyridin-3-carboxaldehyde-O-methyloxime dissolved in 60 cm$^3$ of tetrahydrofuran, 2.46 g of triethylamine is added. The mixture is cooled to 10° C., and 1.9 g of acetyl chloride is added. After 10 minutes at ambient temperature, the triethylamine hydrochloride is filtered off, the solvent is eliminated by evaporation, and the residue is purified by chromatography on silica (eluent: ethyl acetate). After crystallization from hexane, the expected product is obtained, m.p. 69°–70° C.

| Analysis C$_9$H$_{14}$N$_2$O$_3$, HCl | | | | | | | |
|---|---|---|---|---|---|---|---|
| Calculated: | C % | 54.68 | H % | 7.24 | N % | 14.22 |
| Found: | | 54.53 | | 7.12 | | 14.13 |

Product insoluble in water and in 2N sodium hydroxide, soluble in 2N hydrochloric acid.

EXAMPLE 4

Hydrochloride of the propargyl ether of 1-hydroxy-1,2,5,6-tetrahydropyridin-3-carboxaldehyde oxime 8.9 g of pyridin-3-carboxaldehyde-O-2-propynyl oxime N-oxide (prepared from pyridin-3-carboxaldehyde and O-2-propynyl hydroxylamine followed by oxidation, as indicated in J. Het. Chem. 16. 1459 (1979), m.p. 104°–105° C.), is dissolved in 100 cm$^3$ of methanol, then, while maintaning the temperature below 5° C., 4.8 g of sodium borohydride is added and the whole is agitated at ambient temperature for 2 hours, then concentrated under reduced pressure. The residue is taken up with water, extracted with ethyl acetate, dried on sodium sulphate and evaporated under reduced pressure, then chromatographed on silica (eluent: ethyl acetate), and 4.5 g of an oily product is obtained. This is dissolved in ether and salified by the action of a current of gaseous hydrochloric acid. The expected hydrochloride is obtained, a very hydroscopic oil product. After crystallizing from a methanol/ether mixture, 1.2 g of the expected product is obtained in the form of a white powder.

m.p. 132°–135° C. (decomposes) and about 4 g of oil.

| Analysis: | | | | | | |
|---|---|---|---|---|---|---|
| Calculated: | C % | 49.89 | H % | 6.05 | N % | 12.93 |
| Found: | | 49.58 | | 6.16 | | 12.84 |

Soluble in H$_2$O, 2N HCl and 2N NaOH.

EXAMPLE 5

Methyl ether of 1-pivaloyloxy 1-hydroxy-1,2,5,6-tetrahydropyridin-3-carboxaldehyde oxime To a mixture of 0.8 g of methyl ether of 1-hydroxy-1,2,5,6-tetrahydropyridin-3-carboxaldehyde oxime obtained at example 1, in solution in 20 cm$^3$ of tetrahydrofuran and 0.52 g of triethylamine, there is added at 10° C., 0.63 g of pivaloyl chloride. The reaction is continued for 10 minutes at ambient temperature, then the triethylamine hydrochloride is filtered off and the solvent is evaporated under reduced pressure. The residue is chromatographed on silica, eluting with a mixture of benzene and ethyl ether, 1-1, and 0.8 g of the expected product is obtained (unstable during distillation).

| Analysis: C$_{12}$H$_{20}$N$_2$O$_3$ | | | | | | |
|---|---|---|---|---|---|---|
| Calculated: | C % | 59.98 | H % | 8.39 | N % | 11.66 |
| Found: | | 60.06 | | 8.49 | | 11.53 |

EXAMPLE 6

Methyl ether of 1-ethoxy carbonyloxy-1,2,5,6-tetrahydropyridin-3-carboxaldehyde oxime The operation is done as in example 5, starting with 1.4 g of product from example 1, 0.91 g of triethylamine and 0.97 g of ethyl chloroformate. 1.5 g of the expected product is obtained.

| Analysis: C$_{10}$H$_{16}$N$_2$O$_4$ | | | | | | |
|---|---|---|---|---|---|---|
| Calculated: | C % | 52.62 | H % | 7.06 | N % | 12.67 |
| Found: | | 52.42 | | 7.11 | | 12.08 |

EXAMPLE 7

Methyl ether of 1-benzoyloxy-1,2,5,6-tetrahydropyridin-3-carboxaldehyde oxime

To a solution of 1.56 g of the product obtained at example 1 and 1.01 g of triethylamine in 30 cm$^3$ of tetrahydrofuran, cooled to 10° C., 1.41 g of benzoyl chloride is added. The mixture is agitated for 30 minutes at ambient temperature, then taken up with ethyl acetate, washed with water and evaporated to dryness. The residue is purified by chromatographsy on silica (eluent: toluene-ethyl acetate, 8-2), and 1.6 g of the expected product is obtained, crystallized from cyclohexane. m.p. 74°–76° C.

| Analysis: C$_{14}$H$_{16}$N$_2$O$_3$ | | | | | | |
|---|---|---|---|---|---|---|
| Calculated: | C % | 64.6 | H % | 6.20 | N % | 10.76 |
| Found: | | 64.46 | | 6.34 | | 10.72 |

EXAMPLE 8

Hydrochloride of methyl ether of 1-ethoxy-1,2,5,6-tetrahydropyridin-3-carboxaldehyde oxime To a solution of 3 g of the product obtained in example 1 in 50 cm$^3$ of tetrahydrofuran, there is added at 0° C., 0.93 g of 85% sodium hydride. Then, at 0° C., 3 g of ethyl iodide is added, and after leaving to rest for 16 hours, the insoluble matter is filtered off and the remainder is evaporated to dryness. The residue is chromatographed on silica (eluent: ethyl acetate, then methanol-chloroform 3-7), then chromatographed on alumina, eluting with methanol-chloroform (16-1). 1.8 g of residue is obtained which is salified with hydrochloric methanol, and crystallized from ethyl ether. 1.05 g of the expected product is obtained, m.p. 160°–161° C., recrystallized from a mixture of isopropanol and ethyl ether.

| Analysis: C$_9$H$_{16}$N$_2$O$_2$, HCl | | | | | | |
|---|---|---|---|---|---|---|
| Calculated: | C % | 48.98 | H % | 7.76 | N % | 12.69 |
| Found: | | 49.16 | | 7.84 | | 12.85 |

EXAMPLE 9

Methyl ether of 1-ethylamino-carbonyloxy-b 1,2,5,6-tetrahydropyridin-3-carboxaldehyde oxime To a solution of 2 g of the product obtained in example 1 in 20 cm³ of toluene at 20° C., 1.82 g of ethyl isocyanate is added, and the mixture is maintained for 40 minutes at ambient temperature, then evaporated to dryness, and 1.5 g of the expected product is obtained, crystallized from benzene.

| Analysis: $C_{10}H_{17}N_3O_3$ | | | | | | | |
|---|---|---|---|---|---|---|---|
| Calculated: | C % | 52.85 | H % | 7.54 | N % | 18.49 |
| Found: | | 52.96 | | 7.48 | | 18.53 |

EXAMPLE 10

Methyl ether of 1-propyl aminocarbonyloxy-1,2,5,6-tetrahydropyridin-3-carboxyaldehyde oxime The operation is done as at example 9, using 2.1 g of product from example 1 and 2.52 cm³ of propyl isocyanate. 2.85 g of the expected product is obtained. m.p. 110°–111° C., isolated from cyclohexane.

| Analysis: $C_{11}H_{19}N_3O_3$ | | | | | | | |
|---|---|---|---|---|---|---|---|
| Calculated: | C % | 54.76 | H % | 7.94 | N % | 17.42 |
| Found: | | 54.57 | | 7.87 | | 17.19 |

EXAMPLE 11

Methyl ether of 1-isopropylaminocarbonyloxy 1,2,5,6-tetrahydropyridin-3-carboxaldehyde oxime To a solution of 1.2 g of product obtained as in example 1 in 20 cm³ of toluene, 1.54 g of isopropyl isocyanate is added. The mixture is agitated for 4 hours at ambient temperature, then evaporated to dryness, chromatographed on silica (eluent: ethyl acetate-toluene 7-3), and crystallized from hexane. 1.3 g of the expected product is obtained, m.p. 96°–98° C., after crystallizing from cyclohexane.

| Analysis: $C_{11}H_{19}N_3O_3$ | | | | | | | |
|---|---|---|---|---|---|---|---|
| Calculated: | C % | 54.76 | H % | 7.94 | N % | 17.42 |
| Found: | | 54.97 | | 7.86 | | 17.29 |

EXAMPLE 12

Methyl ether of 1-butylaminocabonyloxy 1,2,5,6-tetrahydropyridin-3-carboxaldehyde oxime The operation is done as in example 11, using 1.6 g of product obtained as in example 1, 2.4 cm³ of butyl isocyanate. 1.5 g of the expected product is obtained, m.p. 117°–118° C., after crystallizing from ethyl acetate.

| Analysis: $C_{12}H_{21}N_3O_3$ | | | | | | | |
|---|---|---|---|---|---|---|---|
| Calculated: | C % | 56.45 | H % | 8.29 | N % | 16.46 |
| Found: | | 56.18 | | 8.25 | | 16.28 |

EXAMPLE 13

Methyl ether of 1-phenylaminocarbonyloxy 1,2,5,6-tetrahydropyridin-3-carboxaldehyde oxime The operation is done as in example 9, using 1.25 g of product obtained as in example 1 and 1.75 cm³ of methyl isocyanate. 1.75 g of the expected product is obtained, m.p. 76°–78° C.

| Analysis: $C_{14}H_{17}N_3O_3$ | | | | | | | |
|---|---|---|---|---|---|---|---|
| Calculated: | C % | 61.08 | H % | 6.22 | N % | 15.26 |
| Found: | | 61.15 | | 6.33 | | 15.37 |

EXAMPLE 14

Methyl ether of 1-(4-chlorophenylaminocarbonyloxy)-1,2,5,6-tetrahydropyridin-3-carboxaldehyde oxime The operation is done as in example 9, using 1.5 g of product obtained as at example 1 and 3 g of 4-chlorophenyl isocyanate. 2.84 g of the expected product is obtained, m.p. 142°–144° C. after crystallizing from cyclohexane.

| Analysis: $C_{14}H_{16}ClN_3O_3$ | | | | | | | |
|---|---|---|---|---|---|---|---|
| Calculated: | C % | 54.29 | H % | 5.21 | N % | 13.57 |
| Found: | | 54.08 | | 5.14 | | 13.42 |

EXAMPLE 15

Methyl ether of 1-(4-isopropylphenylaminocarbonyloxy) 1,2,5,6-tetrahydropyridin-3-carboxaldehyde oxime The operation is done as in example 9, using 1.56 g of product obtained as in example 1, and 3.22 g of 4-isopropylphenylisocyanate. 2.8 g of the expected product is obtained. m.p. 115°–117° C., after crystallizing from cyclohexane.

| Analysis: $C_{17}H_{23}N_3O_3$ | | | | | | | |
|---|---|---|---|---|---|---|---|
| Calculated: | C % | 64.33 | H % | 7.31 | N % | 13.24 |
| Found: | | 63.96 | | 7.19 | | 13.06 |

EXAMPLE 16

Methyl ether of 1-paramethoxyphenylaminocarbonyloxy-1,2,5,6-tetrahydropyridin-3-carboxaldehyde oxime The operation is done as in example 9, using 2.1 g of product obtained as in example 1 and 3.5 cm³ of p-methoxyphenyl isocyanate. 2.95 g of the expected product is obtained, m.p. 115°–116° C.

| Analysis: $C_{15}H_{19}N_3O$ | | | | | | | |
|---|---|---|---|---|---|---|---|
| Calculated: | C % | 59.01 | H % | 6.27 | N % | 13.76 |
| Found: | | 59.14 | | 6.22 | | 13.58 |

Operating as in example 9 using appropriated products the compounds of examples 17 to 20 were obtained.

EXAMPLE 17

Methyl ether of 3-chlorophenylaminocarbonyloxy 1,2,5,6-tetrahydropyridin-3-carboxaldehyde oxime m.p. 99°–100° C.

| Analysis: $C_{14}H_{16}ClN_3O_3$ = 309.753 | | | | | | |
|---|---|---|---|---|---|---|
| Calculated: | C % | 54.29 | H % | 5.21 | N % | 13.57 |
| Found: | | 54.07 | | 5.17 | | 13.45 |

EXAMPLE 18

Methyl ether of 3-methoxyphenylaminocarbonyloxy-1.2.5.6-tetrahydropyridin-3-carboxaldehyde oxime m.p. 92°–93° C.

| Analysis: $C_{15}H_{19}N_3O_4$:305.334 | | | | | | |
|---|---|---|---|---|---|---|
| Calculated: | C % | 59.01 | H % | 6.27 | N % | 13.76 |
| Found: | | 59.13 | | 6.31 | | 13.64 |

EXAMPLE 19

Methyl ether of 3,4-dichlorophenylaminocarbonyloxy)-1,2,5,6-tetrahydropyridin-3-carboxaldehyde oxime m.p. 117°–118° C.

| Analysis: $C_{14}H_{15}N_3O_3$ | | | | | | |
|---|---|---|---|---|---|---|
| Calculated: | C % | 48.85 | H % | 4.39 | N % | 12.21 |
| Found: | | 49.03 | | 4.55 | | 12.09 |

EXAMPLE 20

Methyl ether of 1-[[(1R)-1-phenyl-1-ethyl]-aminocarbonyloxy]-1,2,5,6-tetrahydropyridin-3-carboxaldehyde oxime and corresponding (1S) isomer Isomers (1R) and (1S), m.p. 115°–116° C.

| Analysis: $C_{16}H_{21}N_3O_3$ = 303.362 | | | | | | | |
|---|---|---|---|---|---|---|---|
| Calculated: | | C % | 63.35 | H % 6.98 | | N % | 13.85 |
| Found: | isomer (1R) | | 63.48 | 7.12 | | | 13.91 |
| Found: | isomer (1S) | | 63.59 | 6.99 | | | 13.77 |

EXAMPLE OF PHARMACEUTICAL COMPOSITIONS (a) Tablets have been prepared corresponding to the following formula:

Product of example 14: 10 mg

Excipient q.s. for a tablet finished at: 300 mg (detail of excipient: lactose, corn starch, treated startch, rice starch, magnesium stearate, talc).

(b) Capsules have been prepared corresponding to the following formula:

Product of example 14: 20 mg

Excipient q.s. for a capsule finished at: 300 mg (detail of excipient: talc, magnesium stearate, aerosil).

PHARMACOLOGICAL STUDY

Acute toxicity

The test was carried out on male mice ($CD_1$ Charles Rivers), of 22 to 24 g, having fasted for 16 hours. The products are administered by oral route at doses of 1000, 500, 250, 125, 62, 31 and 16 mg/kg. The mortality is noted during the 7 days following the treatment.

The results are reported in the following Table 1.

TABLE 1

| Example | $LD_{50}$ mg/kg |
|---|---|
| 1 | 60 |
| 3 | 100 |
| 4 | 80 |
| 6 | 125 |
| 7 | 90 |
| 10 | 125 |
| 13 | 250 |
| 14 | >1000 |
| 15 | 350 |
| 16 | 60 |
| Arecoline HBr | 600 |

Test of ileum isolated from guinea-pig

Pieces of ileum are removed from guinea-pigs killed by decapitation. The isolated ileum is placed in 10 cm$^3$ of Tyrode solution at 37° C. and aerated with a mixture of oxygen (95%) and carbon dioxide gas (5%). The contractions due to the products are registered by means of a detector connected to a polygraph. The products to be tested are added at concentrations between $1.10^{-3}$M and $1.10^{-8}$M/l.

The products presenting a contracting effect are tested vis-a-vis atropine and hexamethonium in order to establish if the activity is of "muscarine" or "nicotine" type.

The possible antagonist activity of the products is tested vis-a-vis acetylcholine.

The agonist activity is expressed in $pD_2$ (negative logarithm of the dose which produces 50% of the maximum effect).

The antagonist activity is expressed in $DE_{50}$ (dose reducing by 50% the maximum response induced by acetylcholine). The results are reported in the following Table 2.

TABLE 2

| Example | $pD_2$ | $DE_{50}$ mg/kg |
|---|---|---|
| 1 | 5.38 | — |
| 3 | 4.90 | — |
| 4 | 5.24 | — |
| 6 | 4.94 | — |
| 7 | <4 | >1 × 10$^{-4}$ |
| 10 | <4 | >1 × 10$^{-4}$ |
| 13 | <4 | >1 × 10$^{-4}$ |
| 14 | <4 | >1 × 10$^{-4}$ |
| 15 | <4 | >1 × 10$^{-4}$ |
| 16 | <4 | >1 × 10$^{-4}$ |
| arecoline | 6.48 | — |

Diarrhoeic activity

The test is carried out on male mice ($CD_1$ Charles Rivers) weighing 25 to 0 g, after fasting for 6 hours. The product dissolved at 5% in methocel is administered by oral route by means of an oesophage probe.

Control animals receive only the excipient.

After treatment, the animals are placed separately in cages of which the base is covered with blotting paper, and they are put under observation for 30, 60, 120 and 180 minutes.

The sheets of absorbent paper are changed after each observation.

The consistency of the feces is evaluated according to the method of Randall and Baruth (Arch. Int. Pharmacodyn. 220, 94, 1976) according to the following scale of values.

0: consistency firm
1: feces slightly soft, with or without a damp halo
2: feces slightly soft, with a well defined circle of humidity.
3: feces soft with a large circle of humidity.
4: feces without consistency with a very large circle of humidity.

For each product, the dose is noted which causes diarrhoea in 50% of the animals according to the method of Miller and Tainter (Proc. Soc. Exp. Biol. Med., 57, 261, 1944).

The results are reported in the following Table 3.

TABLE 3

| Example | DE$_{50}$ mg/kg |
|---|---|
| 1 | 0.5 |
| 3 | 0.5 |
| 4 | 0.9 |
| 6 | 0.6 |
| 7 | 1.5 |
| 10 | 20 |
| 13 | 5 |
| 14 | 10 |
| 15 | 20 |
| 16 | 6 |
| arecoline | 35 |

Hypothermic activity

The test is carried out on male mice (CD$_1$ Charles RAivers) weighing 25–30 g, having fasted for 6 hours.

The temperature of the body is noted by means of a thermocouple inserted about 1.5 cm in the rectum and connected to an electric temperature recorder.

The products are administered by oral or sub-cutaneous route and the temperatures are noted at the instant 0 and at 30 minutes, 1 hour, 2 hours and 2 and a half hours after treatment.

The degree of hypothermia is evaluated as the difference between the treated animals and the controls, and the dose necessary to reduce the body temperature by 1° C. is noted.

The results are reported in the following Table 4.

TABLE 4

| | Effective dose (−1° C.) in mg/kg | |
|---|---|---|
| Example | O.R. | SC.R |
| 1 | 0.19 | 0.20 |
| 3 | 0.22 | 0.20 |
| 4 | 0.48 | 0.49 |
| 6 | 0.26 | 0.24 |
| 7 | 0.42 | 0.21 |
| 10 | 1.4 | 1.3 |
| 13 | 0.74 | 0.43 |
| 14 | 1.8 | 1.8 |
| 15 | 1.9 | 2.4 |
| 16 | 0.88 | 0.78 |
| arecoline, HBr | 194 | 3 |

Variation of the body temperature

The duration of action of the products is determined, using the doses able to reduce the temperature by 1° to 1.5° C.

See the following Table 5.

TABLE 5

| | | | Variations of the body temperature (°C.) | | | | |
|---|---|---|---|---|---|---|---|
| | Dose | | | Treatment Time in Minutes | | | |
| Example | mg/kg | Administration | 0 | 30 | 60 | 120 | 180 |
| 1 | 0.25 | os | +0.1 | −1.4** | −1.2** | −0.1 | −0.1 |
| | 0.25 | sc | ±0. | −1.4** | −1.1** | −0.1 | −0.1 |
| 3 | 0.25 | os | +0.2 | −1.2** | −0.7** | +0.1 | +0.1 |
| | 0.25 | sc | +0.1 | −1.2** | −0.8** | +0.1 | +0.1 |
| 4 | 0.75 | os | ±0. | −1.6** | −1.0** | ±0. | −0.1 |
| | 0.75 | sc | ±0. | −1.4** | −1.1** | −0.1 | ±0. |
| 6 | 0.35 | os | ±0. | −1.3** | −1.1** | −0.1 | ±0. |
| | 0.35 | sc | ±0. * | −1.4** | −1.1** | −0.1 | +0.1 |
| 7 | 0.5 | os | −0.1 | −1.1** | −0.9** | ±0. | +0.1 |
| | 0.25 | sc | −0.1 | −1.2** | −0.9** | ±0. | +0.1 |
| 10 | 1.56 | os | −0.2 | −1.2** | −1.0** | −0.1 | +0.1 |
| | 1.56 | sc | ±0. | −1.2** | −1.1** | −0.1 | +0.1 |
| 13 | 1. | os | +0.2 | −1.4** | −1.1** | −0.1 | +0. |
| | 0.5 | sc | +0.1 | −1.2** | −1.2** | −0.1 | ±0.1 |
| 14 | 2.5 | os | +0.1 | −1.3** | −1.5** | −0.3** | +0.1 |
| | 2.5 | sc | ±0. | −0.4** | −1.5** | −1.3** | −0.2 |
| 15 | 2. | os | +0.2 | −0.8** | −1.0** | +0. | +0.1 |
| | 4. | sc | +0.2 | −0.5** | −1.5** | −1.5** | −0.3 |
| 16 | 1. | os | +0.1 | −1.1** | −1.1** | −0.1 | ±0. |
| | 1. | sc | ±0. | −1.2** | −1.5** | −0.3* | +0.1 |
| Arecoline, | 200 | os | +0.1 | −1.1** | −1.0** | −0.2 | −0.1 |
| HBr | 3.5 | sc | −0.1 | −1.5** | −0.1 | +0.2* | +0.2 |

**Values significantly different from the controls (p <0.01)
*Values significantly different from the controls (p <0.5)

What is claimed is:

1. Compounds of the formula (I)

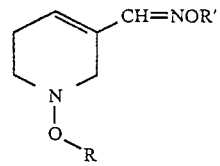

in which R is selected from the group consisting of hydrogen, methyl, ethyl, n-propyl, isopropyl, n-butyl, isobutyl, n-pentyl, n-hexyl, tert-butyl, tert-pentyl, neopentyl, ethylene radical, acetylene radical, cyclopropyl, cyclobutyl, cyclopentyl, cyclohexyl, cyclopropylmethyl, cyclobutylmethyl, cyclopentylmethyl, cyclohexylmethyl, phenyl which is unsubstituted or substituted with halogen, alkyl having up to 8 carbon atoms or alkoxy having up to 8 carbon atoms, —COCH₃,

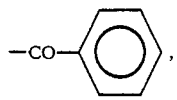

—CONH—R₂ and COR₁,
in which R₁ is selected from the group consisting of methyl, ethyl, n-propyl, isopropyl, n-butyl, isobutyl, alkoxy having up to 8 carbon atoms, n-pentyl, n-hexyl, tert-butyl, tert-pentyl, neopentyl, ethylene radical or acetylene radical, and R₂ is selected from the group consisting of methyl, ethyl, n-propyl, isopropyl, n-butyl, isobutyl, n-pentyl, n-hexyl, tert-butyl, tert-phenyl, neopentyl, ethylene radical, acetylene radical, phenyl which is unsubstituted or substituted with halogen, alkyl having up to 8 carbon atoms or alkoxy having up to 8 carbon atoms, and phenalkyl, which is unsubstituted or substituted with halogen, alkyl having up to 8 carbon atoms or alkoxy having up to 8 carbon atoms, and R' is selected from the group consisting of methyl, ethyl, n-propyl, isopropyl, n-butyl, isobutyl, n-pentyl, n-hexyl, tert-butyl, tert-pentyl, neopentyl, ethylene radical, acetylene radical, cyclopropyl, cyclobutyl, cyclopentyl, cyclohexyl, cyclopropylmethyl, cyclobutylmethyl, cyclopentylmethyl and cyclohexylmethyl.

2. Compounds of the formula (I) as defined in claim 1, in which R represents hydrogen, as well as their addition salts with organic or mineral acids.

3. Compounds of the formula (I) as defined in claim 1, in which R represents the radical —COCH₃, as well as their addition salts with organic or mineral acids.

4. Compounds of the formula (I) as defined in claim 1, in which R represents the radical

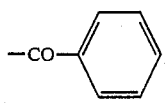

as well as their addition salts with organic or mineral acids.

5. Compounds of the formula (I) as defined in claim 1, in which R represents the radical —CONH—R₂ in which R₂ represents butyl, phenyl, 4-methoxyphenyl, 4-chlorophenyl or 4-isopropylphenyl, as well as their addition salts with organic or mineral acids.

6. Compounds of the formula (I) as defined in any one of claims 1 to 5 in which R' represents the radical —CH₃, as well as their addition salts with organic or mineral acids.

7. Compounds of the formula (I) as defined in any one of claims 1–5 in which R' represents the radical —CH₂C≡CH as well as their addition salts with organic or mineral acids.

8. Methyl ether of (4-chlorophenyl)-aminocarbonyloxy1,2,5,6-tetrahydropyridin-3-carboxaldehyde oxime as well as its addition salts with acids.

9. A therapeutic composition for the treatment of patients suffering from senile dementia, Alzheimer's disease or memory defects in the aged, susceptible to treatment with cholinergics, comprising a central cholinergically effective amount of a compound as defined in claim 1 or its therapeutically acceptable acid addition salt, and a therapeutically acceptable carrier.

10. A method for treating patients suffering from senile dementia, Alzheimer's disease or memory defects in the aged, susceptible to treatment with cholinergics, comprising administering to the patient a central cholinergically effective amount of a compound as defined in claim 1 or its therapeutically acceptable acid addition salt.

* * * * *